United States Patent
Ali et al.

(10) Patent No.: US 11,164,663 B2
(45) Date of Patent: Nov. 2, 2021

(54) MINIMIZING ERRORS IN PRESCRIPTION MEDICATION DISPENSING

(71) Applicant: INTERNATIONAL BUSINESS MACHINES CORPORATION, Armonk, NY (US)

(72) Inventors: Asmahan A. Ali, Highland, NY (US); Ali Y. Duale, Poughkeepsie, NY (US); Mustafa Y. Mah, Highland, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1014 days.

(21) Appl. No.: 15/354,745

(22) Filed: Nov. 17, 2016

(65) Prior Publication Data

US 2018/0137254 A1 May 17, 2018

(51) Int. Cl.
*G16H 10/60* (2018.01)
*G16H 40/63* (2018.01)
*G16H 20/10* (2018.01)

(52) U.S. Cl.
CPC ........... *G16H 10/60* (2018.01); *G16H 20/10* (2018.01); *G16H 40/63* (2018.01)

(58) Field of Classification Search
CPC ........ G06Q 50/22; G06Q 50/24; G06F 19/30; G06F 19/32; G06F 19/326; G06F 19/34; G06F 19/3456; G06F 19/3462; G16H 10/00; G16H 10/60; G16H 20/00; G16H 20/10; G16H 20/13
USPC ........................................ 705/2, 3
See application file for complete search history.

(56) References Cited

U.S. PATENT DOCUMENTS

| | | | |
|---|---|---|---|
| 6,421,650 B1* | 7/2002 | Goetz | G16H 20/10 |
| | | | 705/3 |
| 8,849,449 B2 | 9/2014 | Waugh et al. | |
| 2002/0029223 A1* | 3/2002 | Rice | G16H 20/10 |
| 2004/0172289 A1* | 9/2004 | Kozic | G06Q 10/10 |
| | | | 705/2 |
| 2010/0161353 A1 | 6/2010 | Mayaud | |
| 2013/0085767 A1* | 4/2013 | Kulawiec | G16H 20/10 |
| | | | 705/2 |
| 2013/0090947 A1* | 4/2013 | Nockley | G06F 19/322 |
| | | | 705/3 |
| 2013/0211847 A1 | 8/2013 | Vaidya et al. | |
| 2014/0114470 A1* | 4/2014 | Rashid | G06F 19/00 |
| | | | 700/235 |
| 2015/0254423 A1 | 9/2015 | Schaub | |

(Continued)

OTHER PUBLICATIONS

IBM, Method for reducing errors in prescription and drug interactions by creating a grid enabled prescription registry Database: ip.com; ip.com No. IPCOM000016198D, Published Nov. 23, 2002, pp. 1-2.

*Primary Examiner* — Jason S Tiedeman
(74) *Attorney, Agent, or Firm* — Cantor Colburn LLP; Teddi Maranzano (57) ABSTRACT

Embodiments include method, systems and computer program products for minimizing errors in prescription medication dispensing. Aspects include obtaining, by a processor, a prescription of a medication for a patient. Then, aspects include obtaining, by the processor, a patient profile associated with the patient and obtaining, by the processor, medication details for the medication. Aspects also include displaying to the patient, by a first device, the medication details.

10 Claims, 6 Drawing Sheets

(56) References Cited

U.S. PATENT DOCUMENTS

| | | | |
|---|---|---|---|
| 2015/0310454 A1* | 10/2015 | Ranieri | G16H 20/10 |
| | | | 348/161 |
| 2016/0163034 A1* | 6/2016 | Jacobs | G06K 9/00 |
| | | | 382/142 |
| 2016/0357929 A1* | 12/2016 | Ghouri | G06F 19/3431 |
| 2017/0017774 A1* | 1/2017 | Skoda | H04L 67/42 |
| 2017/0103185 A1* | 4/2017 | Adams | G07F 9/026 |
| 2017/0132867 A1* | 5/2017 | Berg | G16H 70/20 |
| 2017/0161457 A1* | 6/2017 | Meredith | G16H 20/00 |
| 2017/0344724 A1* | 11/2017 | Nockley | G16H 10/60 |
| 2018/0068086 A1* | 3/2018 | Hanson | G08B 23/00 |
| 2019/0279182 A1* | 9/2019 | Rheault | G06Q 20/18 |
| 2020/0335192 A1* | 10/2020 | Tupler | G16H 20/13 |
| 2021/0070548 A1* | 3/2021 | Hawkes | G16H 20/17 |

\* cited by examiner

MINIMIZING ERRORS IN PRESCRIPTION MEDICATION DISPENSING

BACKGROUND

The present disclosure relates to prescription errors, and more specifically, to methods, systems, and computer program products for minimizing errors in prescription medication dispensing.

Prescription medications are used to treat a variety of ailments. Although common, prescription medications can be dangerous if taken by mistake or in combination with other prescription medications. Patient errors in taking prescription medication can contribute to further illness and even death depending on the types of medications being taken. Additionally, a medical professional such as a doctor or pharmacy can make mistakes in prescribing and dispensing medications for patients.

SUMMARY

Embodiments include a computer system for minimizing errors in prescription medication dispensing, the computer system for minimizing errors in taking prescription medication having a processor configured to perform a method. The method includes obtaining, by a processor, a prescription of a medication for a patient. Then, the method includes obtaining, by the processor, a patient profile associated with the patient and obtaining, by the processor, medication details for the medication. The method also includes displaying to the patient, by a first device, the medication details.

Embodiments also include a computer program product for minimizing errors in prescription medication dispensing, the computer program product including a non-transitory computer readable storage medium having computer readable program code embodied therewith. The computer readable program code including computer readable program code configured to perform a method. The method includes obtaining, by a processor, a prescription of a medication for a patient. Then, the method includes obtaining, by the processor, a patient profile associated with the patient and obtaining, by the processor, medication details for the medication. The method also includes displaying to the patient, by a first device, the medication details.

Embodiments also include a method for minimizing errors in prescription medication dispensing. The method includes obtaining, by a processor, a prescription of a medication for a patient. Then, the method includes obtaining, by the processor, a patient profile associated with the patient and obtaining, by the processor, medication details for the medication. The method also includes displaying to the patient, by a first device, the medication details.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

DETAILED DESCRIPTION

In accordance with exemplary embodiments of the disclosure, methods, systems and computer program products for minimizing errors in prescription medication dispensing are provided. The method includes obtaining a prescription for a medication prescribed for a patient. The prescription is then analyzed to determine medication details for the medication. These medication details include color, shape, form, dosage, and the like. The medication details are obtained from a medication database or from the medication manufacturer. The medication details are then sent to the patient so the patient can verify they are taking the correct medication or picking up the correct medication from a pharmacist. For example, after a physician writes a prescription, an image of the medication for the patient can be forwarded to the patient's electronic device to verify the medication when the medication is filled and to verify the medication when the patient takes the medication. In addition to an image, the patient's electronic device can receive medication attributes such as, for example, dosage information, drug interactions, the number of refills allowed, side effects, and the like.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 1:
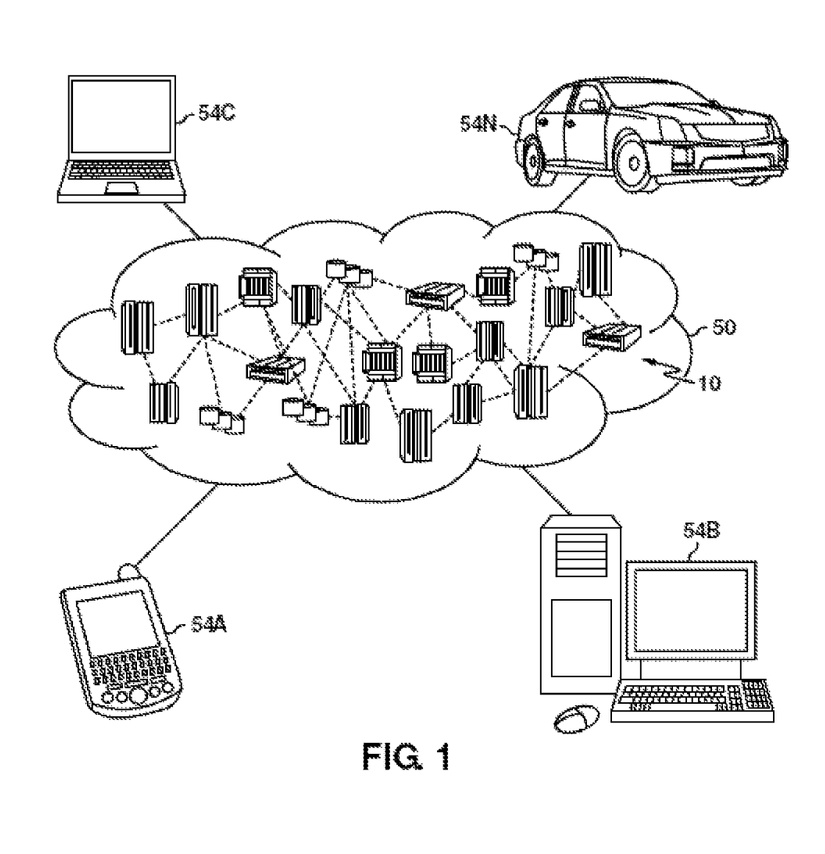
FIG. 1 depicts a cloud computing environment according to an embodiment of the present invention.

Referring now to FIG. 1, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
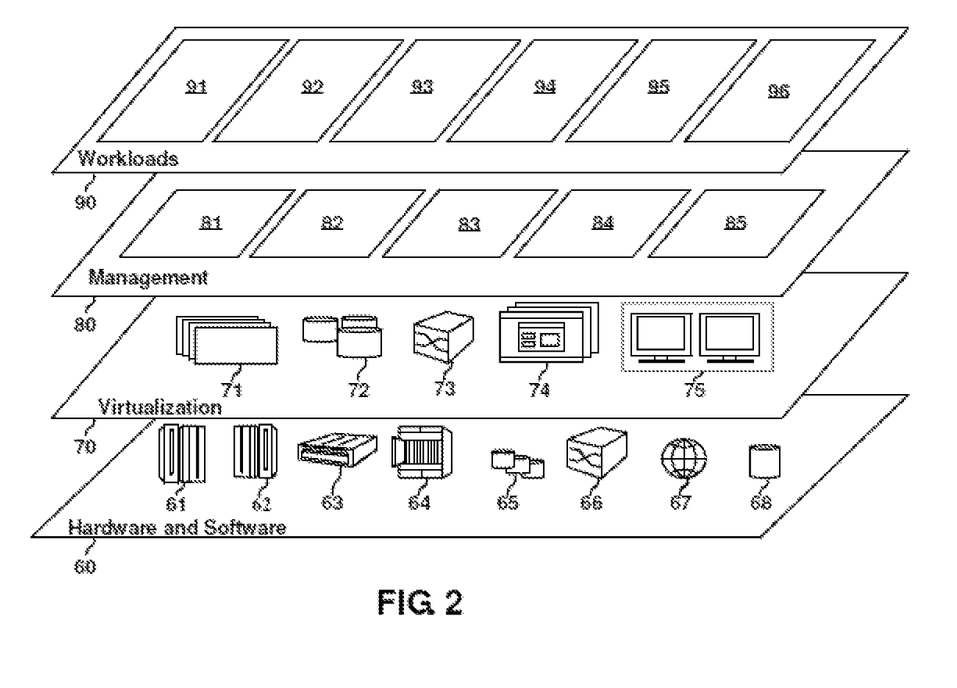
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a virtual pharmacy to minimize prescription errors 96.

Figure 3:
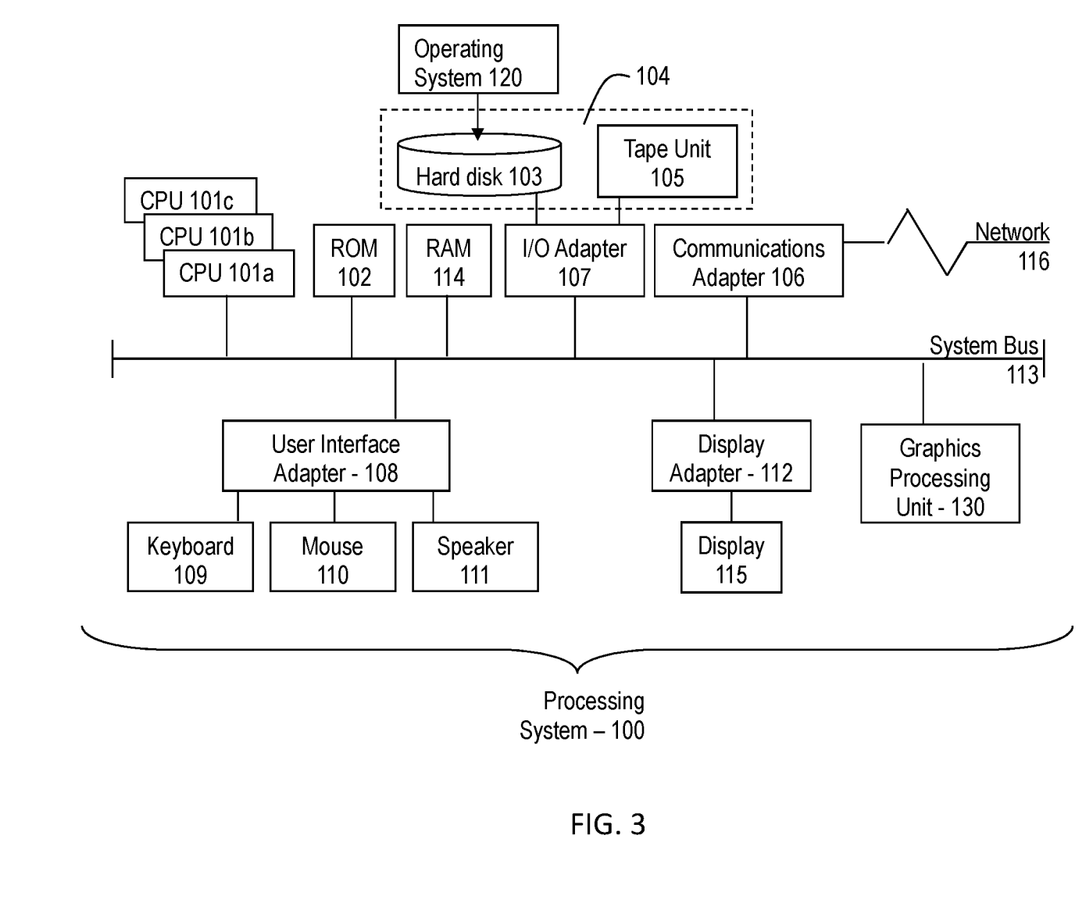
FIG. 3 illustrates a block diagram of a computing system for use in practicing the teachings herein.

Referring to FIG. 3, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 may include a reduced instruction set computer (RISC) microprocessor. Processors 101 are coupled to system memory 114 and various other components via a system bus 113. Read only memory (ROM) 102 is coupled to the system bus 113 and may include a basic input/output system (BIOS), which controls certain basic functions of system 100.

FIG. 3 further depicts an input/output (I/O) adapter 107 and a network adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 may be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which may include a graphics adapter to improve the performance of graphics intensive applications and a video controller. In one embodiment, adapters 107, 106, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which may include, for example, a Super I/O chip integrating multiple device adapters into a single integrated circuit.

In exemplary embodiments, the processing system 100 includes a graphics processing unit 130. Graphics processing unit 130 is a specialized electronic circuit designed to manipulate and alter memory to accelerate the creation of images in a frame buffer intended for output to a display. In general, graphics processing unit 130 is very efficient at manipulating computer graphics and image processing and has a highly parallel structure that makes it more effective than general-purpose CPUs for algorithms where processing of large blocks of data is done in parallel.

Thus, as configured in FIG. 3, the system 100 includes processing capability in the form of processors 101, storage capability including the system memory 114 and mass storage 104, input means such as keyboard 109 and mouse 110, and output capability including speaker 111 and display 115. In one embodiment, a portion of system memory 114 and mass storage 104 collectively store an operating system coordinate the functions of the various components shown in FIG. 3.

Figure 4:
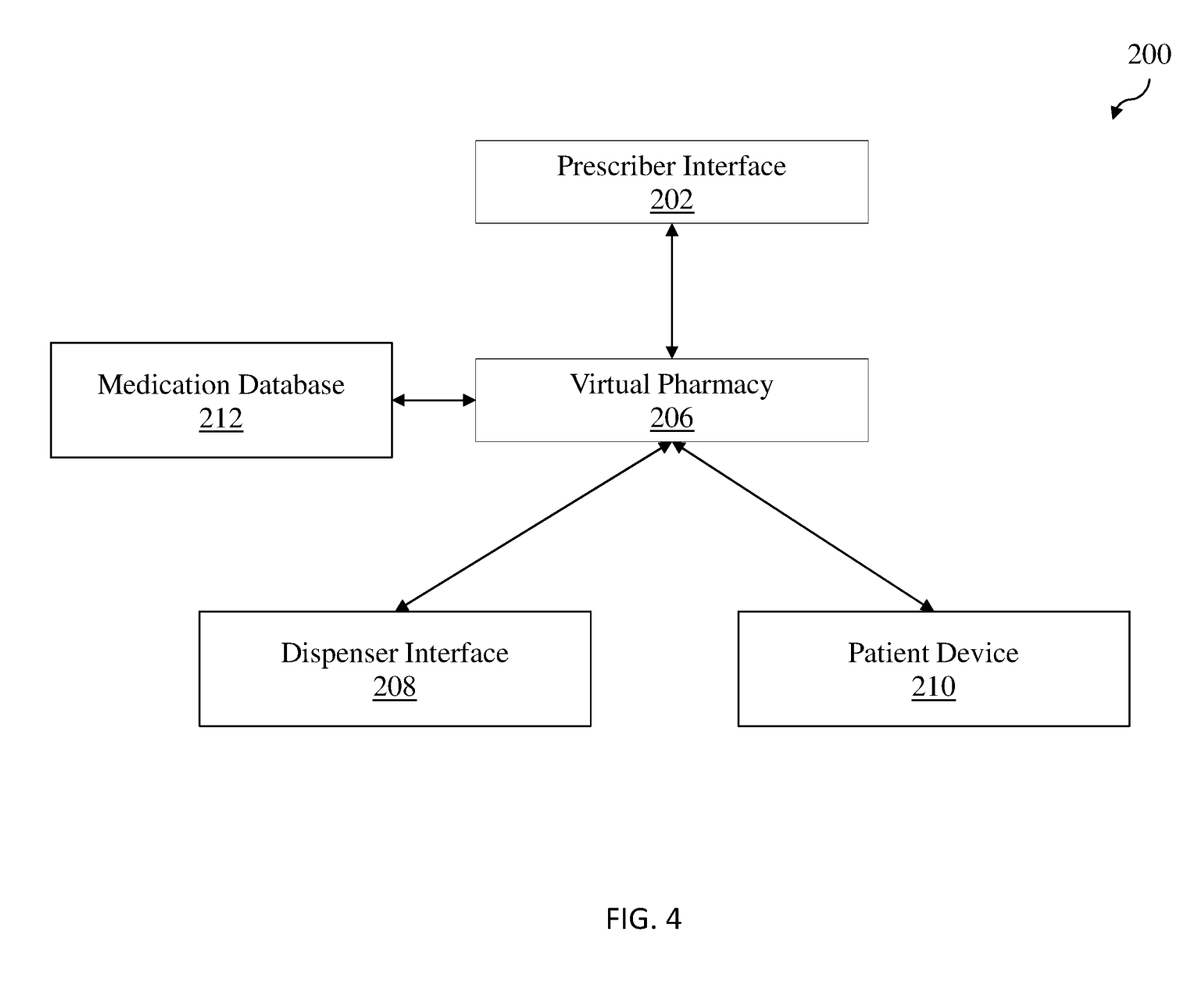
FIG. 4 illustrates a block diagram of a system for minimizing errors in prescription medication dispensing in accordance with an embodiment.

Referring to FIG. 4 there is shown an embodiment of a system 200 for minimizing errors in taking prescription medications according to aspects of the present invention. The system 200 includes a prescriber interface 202, a virtual pharmacy 206, a dispenser interface 208, a patient device 210, and a medication database 212.

The prescriber interface 202 can be an online portal, an application on a cell phone, a dial-in prescription system, and the like. A prescriber can be any medical professional capable of prescribing a medication for a patient such as, for example, a physician, a nurse practitioner, a physician assistant, and the like. The prescriber interface 202 is configured to accept prescription data and connect and send the prescription data to the virtual pharmacy 206.

The virtual pharmacy 206 receives the prescription data and obtains medication data from a medication database 212. The medication database 212 can be a database managed and maintained by a drug manufacturer and can contain information about the medication in the prescription data. For example, the prescription data may contain a prescription for a pill that a patient will need to take once a day to treat an illness. The medication information obtained from the medication database will supply medication attributes for the medication. These attributes can include a description of the medication such as color, shape, form, drug interactions, side effects, dosage recommendations, and the like.

In one or more embodiments, the virtual pharmacy 206 can obtain a patient profile associated with the patient who will be taking the medication. The patient profile can be obtained from the prescriber interface 202, the patient device 210, can be stored in a secure cloud computer environment, or can be stored in the virtual pharmacy 206. The virtual pharmacy 206 compares the medication information to the patient profile to check for any issues such as incorrect dosage or a drug interaction before sending the medication information to the patient device 210. The virtual pharmacy 206 sends the patient device 210 the medication information and attributes to enable the patient to verify receipt of a correct medication when it is picked up from pharmacy dispenser. The patient device 210 can be any electronic device such as, for example, a computer, smartphone, tablet, smartwatch, and the like. The medication attributes can allow the patient to verify the medication is the correct medication before taking the medication.

The dispenser interface 208 receives the prescription data from the virtual pharmacy. In another embodiment, the dispenser interface can receive the prescription data from the prescriber interface or any other prescription system. The dispenser interface 208 can be utilized by any individual or system for dispensing medication such as a pharmacist, a pharmacist technician, or an automated pharmacy dispensing system.

In one or more embodiments, the virtual pharmacy 206 can receive the prescription data from a prescriber of medication. Then, the virtual pharmacy 206 can obtain medication data from the medication database 212 based on the prescription. In addition, a patient profile associated with the patient taking the medication can be obtained. The prescription is compared to the medication information and attributes to check the accuracy of the prescription. For example, if a prescription for a medication that is in liquid form calls for the taking of two pills a day, the virtual pharmacy can send the prescription back to the prescriber to verify the accuracy of the prescription.

In one or more embodiments, the virtual pharmacy 206 can compare the prescription and medication information and attributes to the patient profile obtained from the patient device 210 or from another source to determine whether there are any issues with the prescription. For example, the patient profile can include a medication profile that includes any other medications being taken by the patient. In addition, the patient profile can include a patient medical history. Based upon the patient data and the prescription and medication data, the virtual pharmacy 206 can identify any drug interactions that may be harmful to the patient or any other combination of medical history with the current prescription data that may be harmful to the patient and forward the prescription back to the prescriber for verification of the prescription data.

In one or more embodiment, the virtual pharmacy 206 can assign a grade to the prescription based on a comparison of the prescription to the medication information and attributes and the patient profile. For example, if there are no drug interactions determined based upon the prescribed medication attributes taken from the medication database 212 as compared to a patient medication profile, the virtual pharmacy 206 can assign a high grade for the prescription. If there is a drug interaction, then a low grade can be assigned for the prescription. A threshold grade can be obtained to determine whether a prescription is forwarded to the medication dispenser. For example, if a prescription grade is below the threshold grade, the prescription can be sent back to the prescriber. If the prescription grade is above the threshold grade, the prescription can be forwarded to the medication dispenser.

In one or more embodiments, the patient device 210 can connect to wearable biometric sensors that can be in electronic communication with the patient device 210. Biometric data for the patient can include medical information such as heart rate, blood pressure, blood oxidization, and the like. The virtual pharmacy 206 can analyze the biometric data for the patient to determine whether the prescription conflicts with the biometric data of the patient. For example, if a patient's biometric data is showing a higher than normal blood pressure and the prescription calls for a pain reliever, the virtual pharmacy 206 can determine a potential for a harmful combination and forward the prescription back to the prescriber or assign a low grade or a cautionary grade to the prescription that would require follow up.

In one or more embodiments, the dispenser interface 208 receives the prescription data from the virtual pharmacy 206 or from the prescriber interface 202 directly. When the prescription is filled, the dispenser interface can send a description of the filled prescription to the virtual pharmacy 206. This description can include an image of the filled prescription or attributes such as color, weight, shape, and form. This description can be compared to the medication data from the medication database 212 to determine if the correct medication was filled based upon the prescription data. The virtual pharmacy 206 can notify the patient that a correct medication was filled and include the medication information and attributes in a notice sent to the patient device 210.

In one or more embodiments, the dispenser interface 208 can send a description of the filled prescription to the patient device 210 which include images or other descriptions such as color, weight, shape, and form.

In one or more embodiments, the patient can utilize the patient device to take a picture of the medication and upload the picture to the virtual pharmacy 206. The virtual pharmacy 206 can analyze the image and compare the image to the medical database 212 to determine the medication information and then compare the medication information to the patient profile to determine if the medication is proper for the patient.

In one or more embodiment, the medication attributes can be sent to the patient device 210 and the virtual pharmacy 206 can interact with other applications on the patient device 210. For example, a calendar application may contain a patient's schedule. The schedule can include travel information where the patient may be driving for extended periods of time. Based on the medication attributes, the virtual pharmacy 206 or the patient device 210 can send alerts or warnings to the patient to notify the patient that the medication can cause drowsiness which would affect the patient's driving ability.

Figure 5:
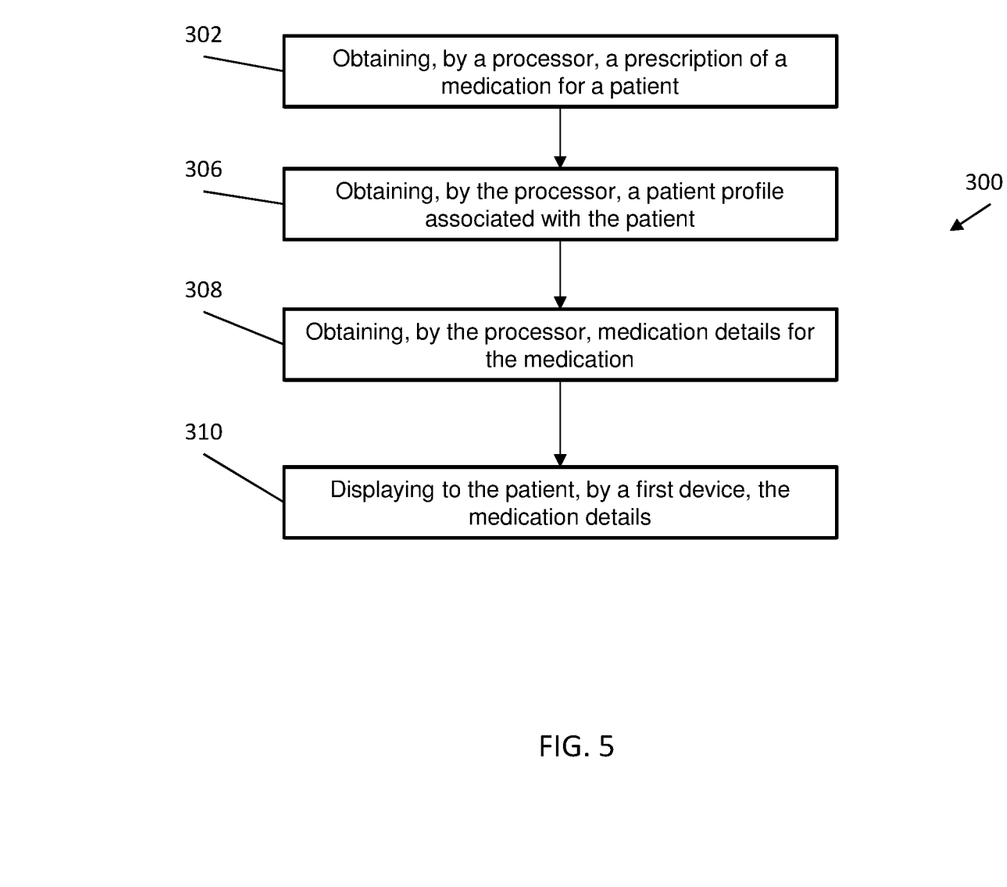
FIG. 5 illustrates a flow diagram of a method for minimizing errors in prescription medication dispensing in accordance with an embodiment.

Referring now to FIG. 5 there is shown a flow diagram of a method 300 for a virtual pharmacy for minimizing prescription errors. At block 302, the method 300 includes obtaining, by a processor, a prescription of a medication for a patient. The method 300 then includes obtaining, by a processor, a patient profile associated with the patient as shown at block 306. At block 308, the method includes obtaining, by a processor, medication details for the medication. And at block 310, the method includes displaying to the patient, by a first device, the medication details.

Additional processes may also be included. It should be understood that the processes depicted in FIG. 5 represent illustrations, and that other processes may be added or existing processes may be removed, modified, or rearranged without departing from the scope and spirit of the present disclosure.

Figure 6:
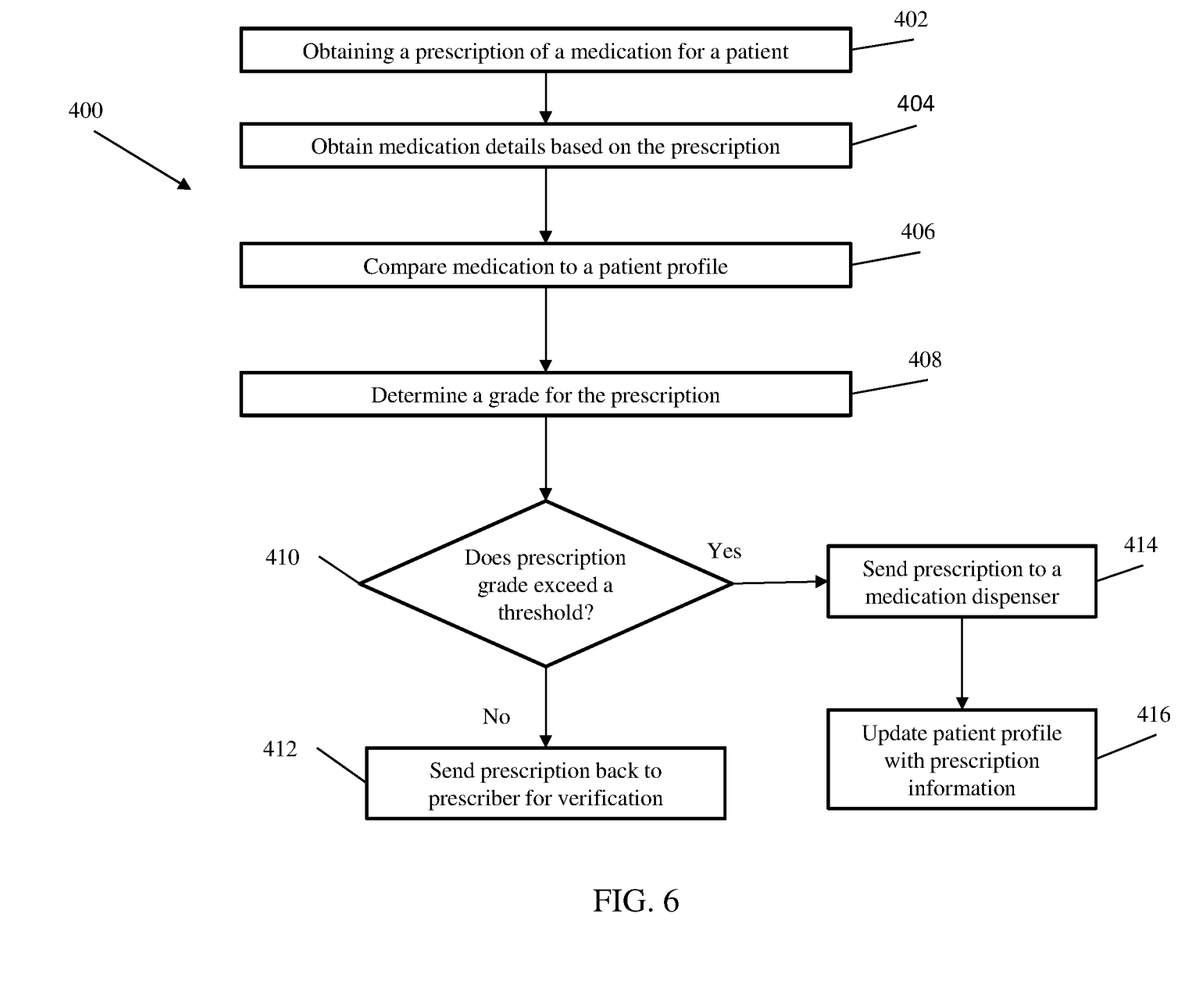
FIG. 6 illustrates a flow diagram of a method for minimizing errors in prescription medication dispensing in accordance with an embodiment.

FIG. 6 is a flow diagram of an exemplary embodiment of a method 400 for minimizing errors in taking prescription medications. At block 402, the method 400 includes obtaining a prescription. The prescription can come from a physician's office or a medical facility. Next, the method 400 obtains medication details about the prescription based upon the received prescription as shown in block 404. The medication details can come from a database of medication or from a physician or from a manufacturer of the medication. The method 400 then compares the medication details to a patient profile at block 406. The patient profile includes information about the patient such as, for example, a medical history and a current and past medication list. The patient profile can also take real-time information from a biometric sensor worn by a patient. After comparing the medication to the patient profile, the method 400 determines a grade for the prescription as shown at block 408. The grade can be any grade such as a letter grade, a color-coded grade, or a numerical grade. In exemplary embodiments, at decision block 410, the method 400 includes determining if the prescription grade is above or below a threshold grade. If the grade for the prescription is above the threshold grade, the method 400 then sends the prescription to a medical dispenser as shown at block 414. And then, at block 416, updates the patient profile to include the new prescription information. If the decision block at 410 determines the prescription grade is below the threshold value, the method 400 sends the prescription back to a prescriber for verification at block 412. The prescriber can verify the prescription and resubmit the prescription after the verification. If the prescriber verifies the prescription, this verification can override a threshold grade to allow for the prescription to be sent to the medication dispenser.

Additional processes may also be included. It should be understood that the processes depicted in FIG. 6 represent illustrations, and that other processes may be added or existing processes may be removed, modified, or rearranged without departing from the scope and spirit of the present disclosure.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD- ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting-data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for minimizing errors in prescription medication dispensing, the method comprising:
    obtaining, by a processor, a prescription of a medication for a patient;
    obtaining, by the processor, a patient profile associated with the patient;
    obtaining, by the processor, medication details for the medication;
    obtaining, from a biometric sensor associated with a user device of the patient, biometric data associated with the patient, wherein the biometric data is one of heart rate data, blood pressure data, or blood oxidation data;
    displaying to the patient, on the user device, the medication details;
    determining a grade for the prescription based on the medication details, the patient profile, and the biometric data;
    obtaining a threshold grade;
    comparing the grade for the prescription to the threshold grade;
    determining a scheduled activity of the patient based on analyzing an application associated with the user device;
    determining a conflict between the medication details for the medication and the scheduled activity of the patient;

sending a notification, to the user device, of the conflict to the patient and displaying the conflict to the patient;

receiving, by the processor, filled prescription data corresponding to the control instructions from the automated medication dispenser comprising medication attributes about a filled prescription, wherein the medication attributes comprise a standard prescription image;

obtaining, by the user device, an image of the filled prescription;

comparing the image of the filled prescription to the standard prescription image;

determining that the medication is incorrect based on the comparing the image of the filled prescription to the standard prescription image; and generating an alert for the patient based the determining that the medication is incorrect;

sending the alert to the user device and displaying the alert to the patient;

rejecting the prescription based upon the grade for the prescription being below the threshold grade;

forwarding the prescription to a prescriber based on the grade for the prescription being less than the threshold grade;

receiving a verification from the prescriber responsive to forwarding the prescription to the prescriber;

forwarding the verification to the automated medication dispenser; and outputting, by the processor, control instructions to cause the automated medication dispenser to dispense the medication to the patient according to the verified prescription.

2. The method of claim 1, further comprising displaying to the patient, by the user device, the grade for the prescription.

3. The method of claim 1, wherein the medication attributes further comprise at least one of a color, a shape, and a weight.

4. The method of claim 1, wherein the patient profile comprises a patient medication profile.

5. The method of claim 1 further comprising:
determining one or more warnings based on the medication details and the patient profile;
displaying, by the user device, the one or more warnings to the patient; and
displaying, by a second device, the one or more warnings to a medication dispenser.

6. The method of claim 1, wherein the grade for the prescription comprises at least one of a numerical grade, a letter grade, or a color-coded grade.

7. A computer system for minimizing errors in prescription medication dispensing, the computer system including a server having a processor, the processor configured to:
obtain a prescription of a medication for a patient;
obtain a patient profile associated with the patient;
obtain medication details for the medication;
obtaining, from a biometric sensor associated with a user device of the patient, biometric data associated with the patient, wherein the biometric data is one of heart rate data, blood pressure data, or blood oxidation data;
display to the patient the medication details;
determining a grade for the prescription based on the medication details, the patient profile, and the biometric data;
obtaining a threshold grade;
com paring the grade for the prescription to the threshold grade;
forwarding the prescription to an automated medication dispenser based upon the grade for the prescription being above the threshold grade, wherein the forwarding includes control instructions that cause the automated medication dispenser to dispense the medication to the patient according to the prescription;
rejecting the prescription based upon the grade for the prescription being below the threshold grade;
forwarding the rejected prescription to a prescriber based on the grade for the prescription being less than the threshold grade;
receiving a verification that the rejected prescription is correct from the prescriber responsive to forwarding the prescription to the prescriber;
forwarding the verification to the automated medication dispenser; and
outputting, by the processor, control instructions that cause the automated medication dispenser to dispense the medication to the patient according to the verified prescription;
determining a scheduled activity of the patient based on analyzing an application associated with the user device;
determining a conflict between the medication details for the medication and the scheduled activity of the patient;
sending a conflict notification, to the user device, of the conflict to the patient which is displayed to the patient;
receiving, by the processor, filled prescription data corresponding to the control instructions from the automated medication dispenser comprising medication attributes about a filled prescription, wherein the medication attributes comprise a standard prescription image;
obtaining, by the user device, an image of the filled prescription;
comparing the image of the filled prescription to the standard prescription image;
determining whether the medication is correct or incorrect based on the comparing the image of the filled prescription to the standard prescription image; and
generating a correctness notification that notifies the patient that the correct medication was filled;
generating an alert for the patient based the determining that the medication is incorrect, and
sending the correctness notification or the alert to the user device which is displayed to the patient.

8. The computer system of claim 7, wherein the processor is further configured to:
determine one or more warnings based on the medication details and the patient profile;
display the one or more warnings to the patient; and
display the one or more warnings to a medication dispenser.

9. A computer program product for minimizing errors in prescription medication dispensing, the computer program product comprising a non-transitory computer readable storage medium having program instructions embodied therewith, the program instructions executable by a processor to cause the processor to perform:
obtaining a prescription of a medication for a patient;
obtaining a patient profile associated with the patient;
obtaining medication details for the medication;
obtaining, from a biometric sensor associated with a user device of the patient, biometric data associated with the patient, wherein the biometric data is one of heart rate data, blood pressure data, or blood oxidation data;
display to the patient the medication details;

determining a grade for the prescription based on the medication details, the patient profile, and the biometric data;

obtaining a threshold grade;

comparing the grade for the prescription to the threshold grade;

forwarding the prescription to an automated medication dispenser based upon the grade for the prescription being above the threshold grade, wherein the forwarding includes control instructions that cause the automated medication dispenser to dispense the medication to the patient according to the prescription;

rejecting the prescription based upon the grade for the prescription being below the threshold grade;

forwarding the rejected prescription to a prescriber based on the grade for the prescription being less than the threshold grade;

receiving a verification that the rejected prescription is correct from the prescriber responsive to forwarding the prescription to the prescriber;

forwarding the verification to the automated medication dispenser; and outputting, by the processor, control instructions that cause the automated medication dispenser to dispense the medication to the patient according to the verified prescription;

determining a scheduled activity of the patient based on analyzing an application associated with the user device;

determining a conflict between the medication details for the medication and the scheduled activity of the patient;

sending a conflict notification, to the user device, of the conflict to the patient which is displayed to the patient;

receiving, by the processor, filled prescription data corresponding to the control instructions from the automated medication dispenser comprising medication attributes about a filled prescription, wherein the medication attributes comprise a standard prescription image;

obtaining, by the user device, an image of the filled prescription;

comparing the image of the filled prescription to the standard prescription image;

determining whether the medication is correct or incorrect based on the comparing the image of the filled prescription to the standard prescription image; and generating a correctness notification that notifies the patient that the correct medication was filled;

generating an alert for the patient based the determining that the medication is incorrect, and sending the correctness notification or the alert to the user device which is displayed to the patient.

10. The computer program product of claim 9, further comprising:

determining one or more warnings based on the medication details and the patient profile;

displaying the one or more warnings to the patient; and displaying the one or more warnings to a medication dispenser.

* * * * *